US010420683B2

(12) United States Patent
Rivas et al.

(10) Patent No.: US 10,420,683 B2
(45) Date of Patent: Sep. 24, 2019

(54) ABSORBENT ARTICLE

(71) Applicant: SCA Hygiene Products AB, Göteborg (SE)

(72) Inventors: Miguel Rivas, Ecatepec de Morelos (MX); Kent Hermansson, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 15/547,573

(22) PCT Filed: Feb. 6, 2015

(86) PCT No.: PCT/SE2015/050132
§ 371 (c)(1),
(2) Date: Jul. 31, 2017

(87) PCT Pub. No.: WO2016/126180
PCT Pub. Date: Aug. 11, 2016

(65) Prior Publication Data
US 2018/0021190 A1    Jan. 25, 2018

(51) Int. Cl.
*A61F 13/15* (2006.01)
*A61F 13/62* (2006.01)
(Continued)

(52) U.S. Cl.
CPC .......... *A61F 13/625* (2013.01); *A61F 5/4401* (2013.01); *A61F 5/485* (2013.01);
(Continued)

(58) Field of Classification Search
CPC ............. A61F 13/625; A61F 13/15756; A61F 13/49061; A61F 13/56; A61F 13/5644;
(Continued)

(56) References Cited

U.S. PATENT DOCUMENTS 4,014,339 A  *  3/1977  Tritsch .................. A61F 13/58
                                                     604/390
4,522,624 A     6/1985  Bolick
(Continued)

FOREIGN PATENT DOCUMENTS

CL      1902-2014      2/2015
CN      1649555 A      8/2005
(Continued)

OTHER PUBLICATIONS

Office Action dated Aug. 4, 2017 issued in corresponding Australian Patent Application No. 2015381885, 2 pages.
(Continued)

*Primary Examiner* — Jacqueline F Stephens
(74) *Attorney, Agent, or Firm* — Drinker Biddle & Reath LLP (57) ABSTRACT

Absorbent article having a longitudinal direction and a transverse direction, a front portion, a rear portion and a middle portion located between the rear portion and the front portion is disclosed. The article has a first longitudinal side edge and a second longitudinal side edge extending in said longitudinal direction, and a first transverse side edge and a second transverse side edge extending in the transverse direction. The article includes a liquid permeable topsheet, a liquid impermeable backsheet, and an absorbent core enclosed between the topsheet and the backsheet, and a first and a second fastening tab attached to said article. The first and second fastening tabs each has a first surface including a first fastener and a second surface including a second fastener.

10 Claims, 5 Drawing Sheets

(51) Int. Cl.
*A61F 13/56* (2006.01)
*A61F 13/58* (2006.01)
*A61F 5/44* (2006.01)
*A61F 5/48* (2006.01)
*A61F 13/49* (2006.01)
*A61F 13/45* (2006.01)

(52) U.S. Cl.
CPC .. *A61F 13/15756* (2013.01); *A61F 13/49061* (2013.01); *A61F 13/56* (2013.01); *A61F 13/5644* (2013.01); *A61F 13/58* (2013.01); *A61F 13/581* (2013.01); *A61F 2013/15056* (2013.01); *A61F 2013/4512* (2013.01); *A61F 2013/49068* (2013.01); *A61F 2013/5661* (2013.01)

(58) Field of Classification Search
CPC ...... A61F 13/58; A61F 13/581; A61F 13/485; A61F 2013/15056; A61F 2013/4512; A61F 2013/49068; A61F 2013/5661; A61F 4/4401; A61F 4/485; A47C 21/06; A47C 21/002; A47C 31/105
USPC .......................................... 604/387, 389, 390
See application file for complete search history.

(56) References Cited

U.S. PATENT DOCUMENTS

| | | | |
|---|---|---|---|
| 4,578,072 A | 3/1986 | Lancaster | |
| 5,019,065 A | 5/1991 | Scripps | |
| 5,087,253 A * | 2/1992 | Cooper | A61F 5/4401 604/385.15 |
| 6,524,294 B1 * | 2/2003 | Hilston | A61F 13/581 604/386 |
| 2002/0032426 A1 | 3/2002 | Lindstrom et al. | |
| 2005/0222552 A1 | 10/2005 | Otsubo | |
| 2006/0004340 A1 | 1/2006 | Ben-Natan | |
| 2008/0086104 A1 | 4/2008 | Karlsson | |
| 2008/0306462 A1 | 12/2008 | Bruckner et al. | |
| 2014/0142533 A1 | 5/2014 | Peltier et al. | |

FOREIGN PATENT DOCUMENTS

| | | |
|---|---|---|
| CN | 101170981 A | 4/2008 |
| EP | 0 732 094 A2 | 9/1996 |
| JP | 2001/309730 A | 11/2001 |
| JP | 2005-312907 A | 11/2005 |
| WO | WO-92/04001 A1 | 3/1992 |
| WO | WO 2012/158538 A2 | 11/2012 |

OTHER PUBLICATIONS

Extended European search report dated Jun. 18, 2018 issued in corresponding European patent application No. 15 88 1331.
Japanese Office Action dated Nov. 8, 2018 issued in corresponding Japanese patent application No. 2017-560461 (2 pages) and its English-language translation thereof (1 page).
Colombian Office Action No. 13910 dated Jan. 7, 2019 issued in corresponding Colombian patent application No. NC2017/0007830 (16 pages) and its partial English-language translation thereof (7 pages).
First Chinese Office Action dated Mar. 29, 2019 issued in Chinese patent application No. 201580075369.1 (8 pages) and its English-language translation thereof (8 pages).

* cited by examiner

ABSORBENT ARTICLE

CROSS-REFERENCE TO PRIOR APPLICATION

This application is a § 371 National Stage Application of PCT International Application No. PCT/SE2015/050132 filed Feb. 6, 2015, which is incorporated herein in its entirety.

TECHNICAL FIELD

The present disclosure relates to an improved absorbent article including a first and a second fastening tab each have a first surface including a first fastening means and a second surface including a second fastening means.

BACKGROUND

Absorbent articles, such as diapers for infants and adults, sanitary napkins, adult incontinence briefs and bed protectors, are well known within the art and used widely. The main purpose of such absorbent articles is normally to absorb, retain and isolate body wastes, i.e., urine, feces, or blood.

Some users are bedridden and laying down in bed for considerable long periods and only getting up from bed for short moments. Other users are in bed during nights and while resting and up out of bed during longer periods. Commonly for them is that when they are lying down in the bed there is a need for protecting the sheets from body liquids and hence a bed protector is used. However, when the user is going up from bed for eating or other activities there is also a need for protecting the cloths of the user from body wastes. Therefore, the care taker/nursing personnel are putting a diaper on the user, when the user is getting up from bed. In such a case, it is necessary to ensure to have both a bed protector and a diaper stored and ready to hand. This requires a storage space for both of the products but also a good planning work. The activity of bringing a diaper and putting on a diaper on a user is also time-consuming for the care taker/nursing personnel.

SUMMARY

In view of the above-it is desired to provide an improved absorbent article that can act as a diaper and/or bed protector.

An aspect relates to an absorbent article having a longitudinal direction and a transverse direction, a front portion, a rear portion and a middle portion located between the rear portion and the front portion. The article having a first longitudinal side edge and a second longitudinal side edge extending in said longitudinal direction, and a first transverse side edge and a second transverse side edge extending in the transverse direction. The article including a liquid permeable topsheet, a liquid impermeable backsheet, and an absorbent core enclosed between the topsheet and the backsheet, and a first and a second fastening tab attached to said article. The first and second fastening tabs each have a first surface including a first fastening means and a second surface including a second fastening means.

The absorbent article according to embodiments of the invention can both act as a diaper and a bed protector which reduces the need of two different kinds of products for the user when the user is laying in the bed and moving up from the bed. By means of the first and second fastening tabs each having a second surface including a second fastening means, the bed protector can easily and securely being fastened to the bed or other supporting material such as a chair. Furthermore, by means of the first and second fastening tabs each having a first surface including a first fastening means, the absorbent article can advantageously and reliably being fastened around the waist of a user and act as a diaper.

The fastening tabs accordingly constitute a fastening system with a dual function since the fastening tabs can both be secured to the bed and to the products itself for being wrapped around the user's waist. Consequently, there is only need for one kind of package on the storage shelf for the combined diaper and bed protector, which saves storage, space and hence costs. Further, this enables the care taker/nursing personnel to save time since the care taker does not need to get another product and change on the user, but only secure the combined diaper and bed protector with the fastening tabs around the user's waist. It is also easy to make the users bed when the user is getting up from bed since the bed protector is naturally removed from bed.

According to an embodiment, the article has a third and a fourth fastening tab attached to said article. The third and fourth fastening tabs each has a first surface including a first fastening means and a second surface including a second fastening means. As a result of having four fastening tabs instead of two fastening tabs attached to the absorbent article, the absorbent article can be fastened safely and securely to the bed without the risk of the absorbent article moving around when the user is laying on it and moving in bed. Furthermore, the flat and open structure of the absorbent article acting as a bed protector, when the user is laying on it on the bed, enhance the air flow around the waist and crotch portion of the user and thus reduces the risk of rashes and skin eruption. Moreover, due to the third and the fourth fastening tab each having a first surface including a first fastening means, the absorbent article can be secured safely around the user's waist and hence achieve a secure fit and enhance the fit of the absorbent article acting as a diaper.

According to a further embodiment, at least one of said fastening means is an adhesive.

According to a further embodiment, both of said first and second fastening means is an adhesive.

According to an embodiment, said first fastening means is a mechanical fastening material and said second fastening means is an adhesive.

According to an embodiment, at least one of said first and second fastening means is a mechanical fastening material.

According to a further embodiment, at least one of said first and second fastening means is covered by a release paper. This reduces the risk of the fastening means sticking to other surfaces before the fastening tab is used for securing the article to the bed or for securing the article around the waist of the user.

According to an embodiment, at least one of said first, second, third and fourth fastening tabs have a longitudinal direction Y1 extending in the transverse direction X of the article and a transverse direction X1 extending in the longitudinal direction of the article and a z-direction Z that is orthogonal to said longitudinal Y1 and transverse X1 directions. The fastening tab has a first longitudinal side edge and second longitudinal side edge extending in the longitudinal direction of the fastening tab, and a first transverse side edge and a second transverse side edge extending in the transverse direction of the fastening tab and an imaginary straight line L1 extending in the transverse direction of the fastening tab. Said fastening tab is folded along said imaginary line L1 forming a double-folded fastening tab. The double-folded fastening tab including a first layer positioned on top of a second layer in said z-direction. The first layer having a first surface intended to face towards a user when the absorbent article is in a first position and a second surface intended to face away from the user when the absorbent article is in a first position. The second layer having a first surface intended to face towards a user when the absorbent article is in a first position and a second surface intended to face away from the user when the absorbent article is in a first position.

A z-direction is by definition a direction that is orthogonal to both the longitudinal (Y) and transverse (X) directions. Accordingly, in this context it is in the direction of the thickness of the absorbent article.

Orthogonality is by definition the relation of two lines at right angles to one another, that is perpendicularity.

A first position of the absorbent article is by definition in this context when the absorbent article is used as a bed protector and hence being placed on a flat supported area. Accordingly, the absorbent article is not attached around the waist of a wearer when the absorbent article is in a first position.

To avoid problems associated with the stickiness of the adhesive surface during storage and transport of the absorbent article, the securing adhesive may be protected by a separate detachable strip of paper or the like, a release paper, which has been treated with a release agent. When the absorbent article is to be used, the release paper is removed so that the adhesive is exposed and can be used for securing the absorbent article to the bed or around the waist of a user. The release paper fulfils no other function and is thrown away once it has been detached from the securing adhesive. The use of such release paper involves a number of disadvantages such as higher material and production costs and the need of a disposal of the release paper when removing it from the article. However, by folding the fastening tab along an imaginary line L1 forming a double-folded fastening tab which includes a first layer positioned on top of a second layer, the need of a release paper covering the first fastening means is reduced. If for instance, the second surface of the first layer includes an adhesive, the first surface of the second layer of the fastening tabs may act as a release paper, that is, covering and protecting the second surface of the first layer.

According to a further embodiment, said second surface of the first layer includes said first fastening means.

According to an embodiment, said second surface of the second layer includes said second fastening means.

According to an embodiment, at least one of said fastening tabs have a second imaginary line L2 extending in said transverse direction X1 of the fastening tabs. Said fastening tab is folded along said imaginary line L2. The fastening tab includes a third layer positioned below said second layer in said z-direction and a fourth layer positioned below said third layer in the z-direction. The third layer having a first upper surface and a second lower surface defined in said z-direction. The fourth layer having a first upper surface and a second lower surface defined in said z-direction of the article. By the fastening tab being folded along a second imaginary line L2 so that the fastening tab includes a third and a fourth layer, the stickiness of the adhesive surface of the second fastening means during storage and transport of the absorbent is reduced. Accordingly, the need of a release paper for covering and protecting the second fastening means is decreased.

BRIEF DESCRIPTION OF THE DRAWINGS

Embodiments of the present invention will now be described in more detail with reference to the accompanying schematic drawings:

FIG. 4a illustrates schematically a cross-sectional view of a fastening tab being folded in a package position;

FIG. 4b illustrates schematically a cross-sectional view of a fastening tab being unfolded from the package position to a first position;

FIG. 4c illustrates schematically a cross-sectional view of a fastening tab being in a first position attached to a bed;

FIGS. 6a-6d illustrates schematically the steps of the fastening tab being in a first position and going to a second position fastened to itself around the waist of a user;

DETAILED DESCRIPTION OF PARTICULAR EMBODIMENTS

The absorbent article includes a liquid permeable top sheet, a liquid impermeable backsheet, and an absorbent core enclosed between the top sheet and the backsheet.

The topsheet and the backsheet of the absorbent article may extend together laterally outside of the absorbent core along the whole circumference of the absorbent core and be connected to each other in an edge joint around the periphery of the absorbent core. The backsheet may cover part of the topsheet to form an edge barrier. The edge joint may be faulted in any suitable manner as known in the art such as by means of adhesive, ultrasonic bonding, thermo-bonding, stitching, etc. Alternative covering arrangements such as wrapped-around covers are also conceivable. Furthermore, alternatively, a liquid acquisition layer may be positioned between the topsheet and the backsheet and may extend to the two longitudinal side edges of the absorbent article.

The topsheet may be formed of any material which is suitable for the purpose, i.e. be soft and liquid pervious. Examples of commonly found topsheet materials are nonwoven materials, perforated plastic films, plastic or textile mesh, and fluid permeable foam layers. Laminates including two or more topsheet materials are also commonly employed, as are topsheets including different materials within different parts of the fluid permeable wearer-facing surface.

The backsheet is commonly fluid impermeable. However, backsheet materials that are only fluid repellant may be used, particularly in instances where relatively small amounts of fluid are expected to be taken up. The backsheet is commonly constituted by a thin, flexible, fluid-impermeable plastic film, but fluid-impermeable nonwoven materials, fluid impermeable foams and fluid impermeable laminates are also contemplated. The backsheet may be breathable, implying that air and vapor may pass through the backsheet. Alternatively, the backsheet may not be breathable. Furthermore, the backsheet may have an outer, garment-facing surface of a textile material such as nonwoven.

The absorbent core may be made up of any suitable absorbent or fluid uptake material as known in the art, such as one or more layers of cellulose fluff pulp, foam, fiber waddings, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibers may be pulp fibers and the superabsorbent material may be polyacrylate-based particles.

The absorbent core may further incorporate components for improving the properties of the absorbent core. Some examples of such components are binder fibers, fluid-dispersing materials, wetness indicators, fluid acquisition materials, etc., as known in the art.

The absorbent article, typically in case of a combined bed protector and diaper, can have an elongate, generally rectangular shape when fully extended in all directions. In this context, a generally rectangular shape is intended to encompass also that, for instance, the corners of the absorbent article may be rounded, or that the edges of the absorbent article may not be completely linear. Accordingly, any suitable shape may be used for the absorbent article, such as hourglass shape, trapezoidal shape, triangular shape an oval shape, etc. The shape of the article may be symmetrical about a transverse center line through the article, or may be asymmetrical with end portions having differing shapes and/or differing sizes.

The absorbent article may have two longitudinal side edges having equal length and extending generally in the same direction as a longitudinal center line through the absorbent article. Front and rear end edges can extend transversely to the longitudinal center line at the ends of the absorbent article. The rear end edge is intended to be oriented rearwards during use of the absorbent article, and the front end edge is intended to be facing forwards towards the abdomen of the wearer.

The absorbent article may have a front end portion, a rear end portion and a middle portion located intermediate the end portions, the middle portion being a portion, which is intended to be placed against the crotch of a wearer when the article is used as a diaper and to constitute the main acquisition area for body fluid that reaches the absorbent article.

Further, the absorbent article has fastening tabs with fastening means for fastening of the absorbent article to a supporting surface, such as a bed, or for fastening the absorbent article to itself around the waist of a user. When the absorbent article is secured around the waist of a user, the fastening means is accordingly secured to the article itself, such as the backsheet of the article, and the article is achieved in a second position. When the absorbent article is fastened as a bed protector to a supporting surface, such as a bed, the absorbent article is in a first position. The fastening tabs may be in the form of two longitudinally extending bands and may include fastening means of pressure sensitive adhesive or of a mechanical fastener. Examples of mechanical fasteners are hook-type fasteners, clips, press studs, etc. Combinations of different types of fasteners are also conceivable. When the mechanical fastening material is a hook surface structure, the hooks can engage with a loop surface structure of the article, for example of the backsheet of the article. Accordingly, the backsheet of the absorbent article may be of a loop material for releasably engage with the hook material of the fastening means.

The fastening tab may have an elongate, generally rectangular shape with a first and a second longitudinal side edge extending in the longitudinal direction of the fastening tab and a first and a second transverse side edge extending in the transverse direction of the fastening tab. The first and second longitudinal side edges of the fastening tab may be between 1 cm and 10 cm and the first and second transverse side edges may be between 1 cm and 5 cm. The longitudinal side edges and the transverse side edges of the fastening tab may have the same size and dimension and hence the fastening tab has an essentially quadratic shape.

The fastening tabs may be arranged on the garment-facing surface of the backsheet or on the body-facing surface of the topsheet. The fastening tabs may alternatively be arranged between the topsheet and the backsheet of the absorbent article. Alternatively, the fastening tabs may be arranged to both the backsheet and topsheet at the same time.

The fastening tabs may be inelastic or partly elastic. Herein, "partly elastic tabs" means that certain parts of the tabs have elastic properties, while certain other parts of the tabs do not have elastic properties.

When the fastening means on the fastening tabs includes an adhesive, any suitable adhesive pattern may be used such as full coating of the surface of the fastening tab, one or more longitudinal adhesive band, transverse bands, dots, circles, curves, stars, etc.

Examples of an adhesive tape that could be used as a fastening means is E4462 from supplier Avery Dennison, in Belgium. E4462 is a pre-combined pressure sensitive tape made of polypropylene.

The fastening means can be covered by a releasable protective layer, that is, a release paper. The release paper could for example be a siliconized paper, a nonwoven or any other releasable material as is known in the art. Before placing the absorbent article on the supporting surface such as a bed, the release paper is removed from the fastening means to expose the adhesive and make it available for fastening to the bed. This is also applicable when the article is used as a diaper, before the diaper is secured around the waist of the user, the release paper is removed from the fastening means to expose the adhesive and make it available for fastening to the backsheet of the absorbent article itself.

The fastening tabs may be a one layer fastening tab including a first and a second surface. Further, the fastening tabs may be folded around an imaginary line L1 extending in the transverse direction of the tab to form a double-folded fastening tab including a first layer and a second layer. The double-folded fastening tab may consist of one material in one piece, or may include two pieces of material joined together to form a single piece of material, or may include three or four different pieces of material joined together to form a single piece of material. The first layer of the double-folded fastening tab may include a first surface and a second surface. The first and second layer may be of the same size and dimension so as to overlap each other completely. Alternatively, the first layer and the second layer of the fastening tabs may have different sizes and dimensions so as to partly overlap each other. The fastening tab may be folded upwards in the z-direction to form a double-folded fastening tab wherein the first and second layer is positioned on top of each other and joined together in a transverse side edge of each first and second layer. Alternatively, the fastening tab may be folded downwards in the z-direction to form a double-folded fastening tab wherein the first and second layer is positioned on top of each other and joined together in a transverse side edge of each first and second layer.

The fastening tab may be folded a second time along a second imaginary line L2 extending in the transverse direction of the tab, to form a fastening tab including a first, a second, a third and a fourth layer which is defined as a package position of the fastening tab. The fastening tab may be folded the second time around the longitudinal side edge of the absorbent article and downward in a z-direction and hereby sandwich the absorbent article, that is, the topsheet, backsheet and the absorbent core between the two uppermost layers of the fastening tab (the first and the second layer) and the two lowest layers of the fastening tab (the third and the fourth layer). The third and fourth layer may have each a first and a second surface.

An embodiment of the invention will now be described by means of example referring to the accompanying figures. In this example, the absorbent article can act like a bed protector 1 and/or a diaper 1.

Figure 1:
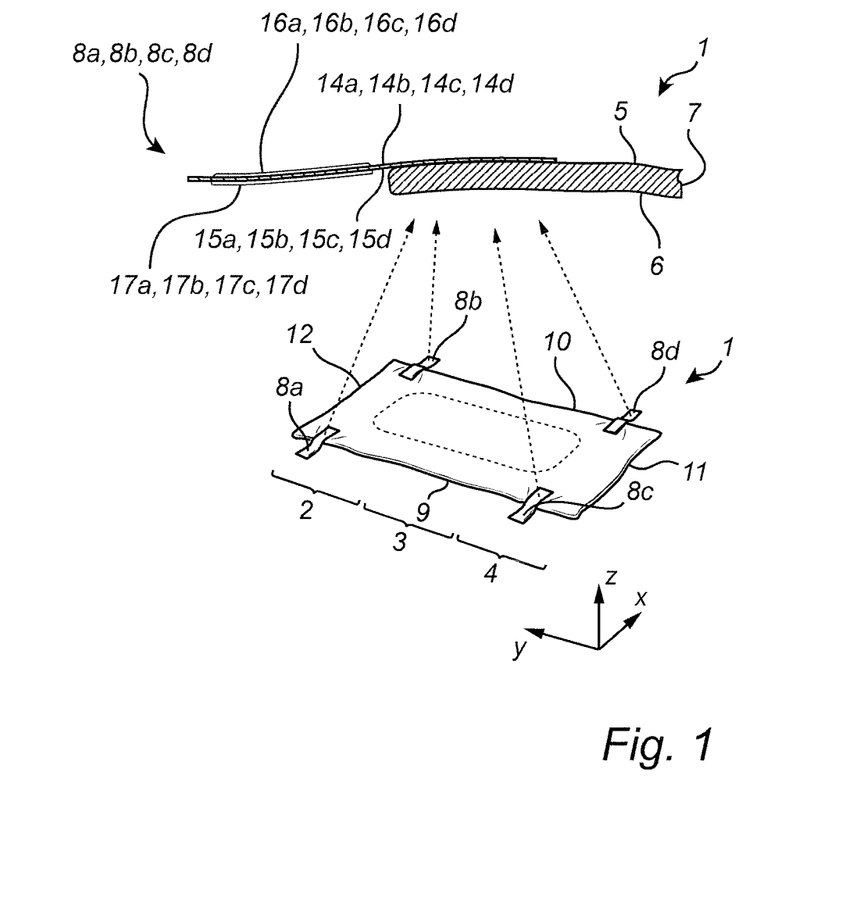
FIG. 1 shows schematically a perspective view of an absorbent article, when the absorbent article is in a first position, and an enlarged cross-sectional view of a fastening tab attached to the absorbent article.

FIG. 1 shows schematically a perspective view of an absorbent article 1 in its first position where it can be used as a bed protector and/or diaper. As used herein, the term "diaper" means an absorbent article which is used for baby care and/or for adult incontinence care. The wearer of the absorbent article is not included in the figure. FIG. 1 is seen from the surface of the absorbent article 1 that is intended to be facing towards a user's body when the article is used as a bed protector and/or a diaper. The article 1 has a transverse direction X, a longitudinal direction Y and a z-direction. The z-direction is defined as the general direction of the thickness. The article 1 further has a front portion 2, a middle portion 3 and a rear portion 4 arranged in the article's longitudinal direction Y. When the article 1 is used as a diaper, that is, attached to itself around the waist of the user, the front portion 2 of the article 1 is intended to cover the pubic region of the user. The middle portion 3 of the article 1 is located adjacent to the front portion 2 in the longitudinal direction Y. When the article 1 is used as a diaper, the middle portion 3 lies between the legs of the user and covers the user's genital region. The rear portion 4 is located at the opposite end of the article 1 from the front portion 2 and is located adjacent to the middle portion 3 in the longitudinal direction Y. When the article 1 is used as a diaper, the rear portion 4 extends towards the user's rear. Furthermore, the absorbent article 1 includes a fluid permeable topsheet 5, disposed at the top surface of the absorbent article 1 which is intended to be facing of the absorbent article 1, a fluid impermeable backsheet 6 disposed at the lower back side of the absorbent article 1 that is intended to be facing the undergarment of the user or the bed surface of the bed, and an absorbent core 7, enclosed between the topsheet 5 and the backsheet 6. The absorbent article 1 further has a first longitudinal side edge 9 and a second longitudinal side edge 10 extending in the longitudinal direction Y. The article has a first transverse side edge 11 and a second transverse side edge 12 extending in the transverse direction X of the article 1. The absorbent article 1 further has four fastening tabs 8a, 8b, 8c, 8d for releasably fastening or securing of the absorbent article 1 to a bed or to itself around the waist of a user. The first fastening tab 8a is arranged to the first longitudinal side edge 9 in the front portion 2 of the article 1. As used herein, the expression "arranged to the longitudinal side edge" means that the fastening tab 8a-d may be extending over the longitudinal side edge so as to be attached to the surface (such as the backsheet 6 or the topsheet 5 or sandwich between the backsheet 6 and the topsheet 5) of the absorbent article 1. The second fastening tab 8b is arranged to the second longitudinal side edge 10 in the front portion 2. The third fastening tab 8c is arranged in the rear portion 4 of the article 1 to the first longitudinal side edge 9 and the fourth fastening tab 8d is arranged in the rear portion 4 to the second longitudinal side edge 10. FIG. 1 further shows a fastening tab 8a, 8b, 8c, 8d in an enlarged cross-sectional view. The fastening tabs 8a, 8b, 8c, 8d are arranged at the topsheet 5 of the article 1 and each fastening tab 8a-d has a first surface 14a-d, respectively, including a first fastening means 16a-d, respectively, which may be an adhesive or a mechanical fastening material. Each fastening tab 8a-d also includes a second surface 15a-d, respectively, including a second fastening means 17a-d, respectively, which may be an adhesive or a mechanical fastening material. In this embodiment, the first surface 14a-d, respectively, is intended to face the user when the article 1 is acting as a diaper 1 and a bed protector 1 and the second surface 15a-d, respectively, is intended to face away from the user when the article 1 is acting as a diaper 1 and a bed protector 1. Before use, the fastening means 16a-d and 17a-d, respectively, may be covered by a removable protective layer 13 (not shown in the drawings) of release-agent-treated paper, plastic film or the like, intended to protect the fastening means against being stuck to surfaces unintentionally or in any way distorted.

Figure 2A:
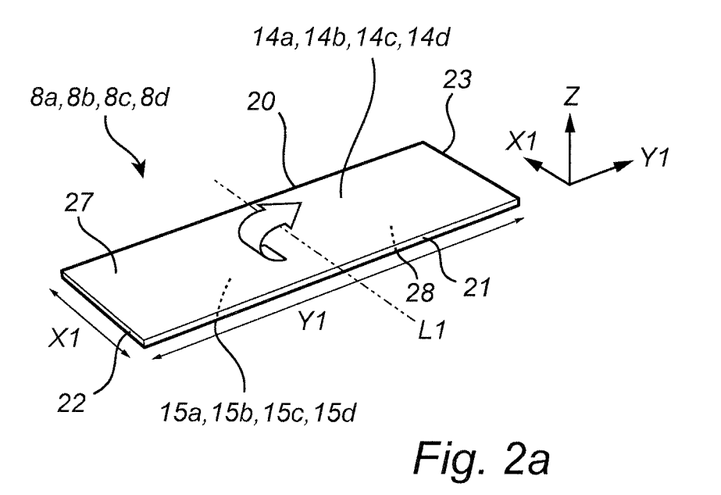
FIG. 2a shows schematically a perspective view of a fastening tab.

FIG. 2a shows schematically a perspective view of a fastening tab 8a, 8b, 8c, or 8d. The fastening tab 8a-d has a longitudinal direction Y1, a transverse direction X1 and a z-direction that is orthogonal to the longitudinal and transverse direction. The fastening tab 8a-d has a first longitudinal side edge 20 and a second longitudinal side edge 21 extending in the longitudinal direction Y1 of the fastening tab 8a-d. The fastening tab 8a-d has a first transverse side edge 22 and a second transverse side edge 23 extending in the transverse direction X1 of the fastening tab 8a-d. An imaginary straight line L1 is extending in the transverse direction X1 of the fastening tab 8a-d. The fastening tab 8a-d may be folded around the imaginary line L1 for forming a double-folded fastening tab 8a-d as disclosed in FIGS. 2b, 4b, 4c and 6a. The fastening tab 8a-d has a first surface 14a-d and a second surface 15a-d, respectively. The first 14a-d and second 15a-d surfaces include fastening means 16a-d, 17a-d, respectively, however they are not shown in FIG. 2a. The arrow in FIG. 2a indicates how the fastening tab 8a-d will be folded to form a double-folded fastening tab 8a-d, that is, around the X1 axis upwardly in the z-direction.

Figure 2B:
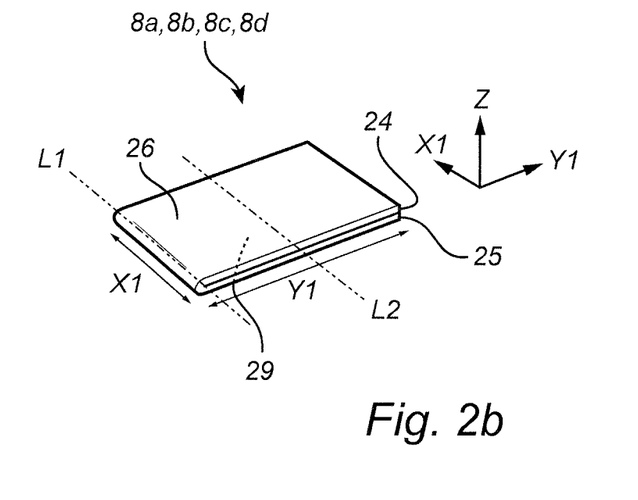
FIG. 2b shows schematically a perspective view of a double-folded fastening tab.

FIG. 2b shows schematically a perspective view of a double-folded fastening tab 8a, 8b, 8c, or 8d. The fastening tab 8a-d has a longitudinal direction Y1, a transverse direction X1 and a z-direction that is orthogonal to the longitudinal and transverse direction. The fastening tab 8*a-d* is folded along the imaginary line L1 thus forming a double-folded fastening tab 8*a-d* including a first layer 24 and a second layer 25. The first layer 24 has a first surface 26 which is the upper surface in the z-direction, and a second surface 27 which is the lower surface in the z-direction (not shown in FIG. 2*b*) facing the first surface 28 (not shown in FIG. 2*b*) of the second layer 25. The second layer 25 has a first surface 28 (not shown in FIG. 2*b*) which is the upper surface in the z-direction and a second surface 29 which is the lower surface in the z-direction. Accordingly, the first surface 26 of the first layer 24 is a subset of the first surface 14*a-d* according to FIG. 2*a* and the second surface 29 of the second layer 25 is a subset of the first surface 14*a-d* according to FIG. 2*a*. A second imaginary line L2 extends in the transverse direction of the fastening tab 8*a-d*. The fastening tab 8*a-d* may be folded along the imaginary line L2 forming a fastening tab 8*a-d* being in a package position and including four layers in accordance with FIGS. 3, 4*a* and 6*b*.

Figure 3:
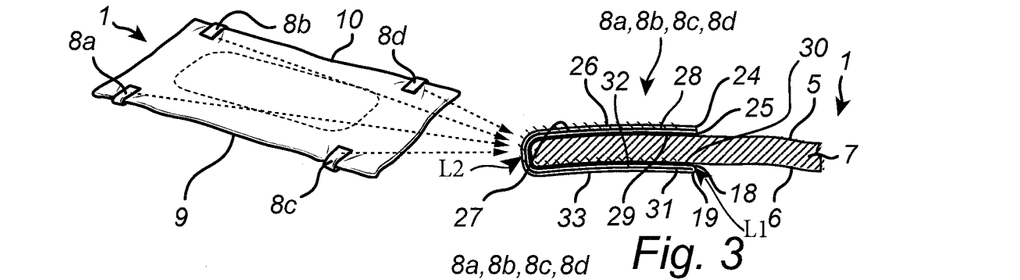
FIG. 3 shows schematically a perspective view of an absorbent article and an enlarged cross-sectional view of a fastening tab arranged to the absorbent article, the fastening tab being in a package position.

FIG. 3 shows schematically a perspective view of an absorbent article 1 and an enlarged cross-sectional view of a fastening tab 8*a-d* being in a package position folded around the longitudinal side edges 9, 10 of the absorbent article 1. The fastening tabs 8*a*, 8*b*, 8*c*, 8*d* are arranged at the topsheet 5 of the article 1 and include a first layer 24 positioned on top of a second layer 25 and a third layer 18 positioned below said second layer 25 and on top of a fourth layer 19. Hence the fastening tabs 8*a-d* are in the package position folded firstly a first time along the imaginary line L1 (shown in FIG. 2*a*-2*b*) creating a double-folded fastening tab 8*a-d*, and secondly a second time along the imaginary line L2 (shown in FIG. 2*b*) as to create a package position. In the package position according to this embodiment, the fastening tabs 8*a-d* are folded along the imaginary lines twice and hence create a first 24, a second 25, a third 18 and a fourth 19 layer that have the same size and dimension and therefore are totally overlapping each other. In this context, the same size and dimension is meant that each layer 24, 25, 18, 19 has the same length of their respectively longitudinal 20, 21 and transverse 22, 23 side edges. However, the fastening tabs 8*a-d* may be folded along said imaginary lines L1 and L2 to create a first 24, a second 25, a third 18 and a fourth 19 layer not having the same size and dimension respectively, for example that is overlapping each other only partly. The fastening tabs 8*a-d* are folded a second time along said imaginary line L2 around the longitudinal side edges 9, 10 of the article 1. By this way, the third layer 18 and the fourth layer 19 of the fastening tabs 8*a-d* are positioned below the absorbent article 1 in the z-direction. The first layer 24 has a first surface 26 intended to face towards a user when the article 1 is in a first position and a second surface 27 intended to face away from the user when the article 1 is in a first position. A first fastening means 16*a-d* (shown in FIG. 6*b*), respectively, is arranged on the second surface 27 of the first layer 24. The second layer 25 has a first surface 28 which is the upper surface in the z-direction and a second surface 29 which is the lower surface in z-direction. The third layer 18 has a first upper surface 30 and a second lower surface 31 defined in the z-direction. The fourth layer 19 has a first upper surface 32 and a second lower surface 33, defined in said z-direction. A second fastening means 17*a-d*, respectively, is arranged on the first surface 30 of the third layer (as shown in FIG. 4*b-c*).

Figures 4A, 4B:
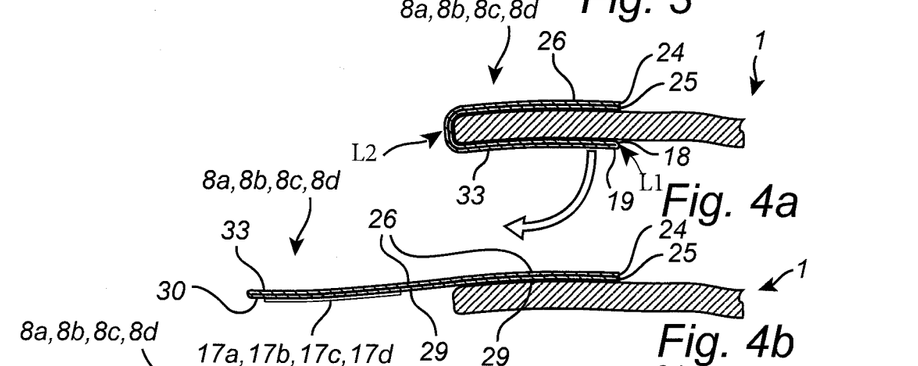
FIGS. 4a-4c illustrates schematically the steps of the fastening tab going from a package position to be secured to a bed when the absorbent article acting as a bed protector.
Figure 4C:
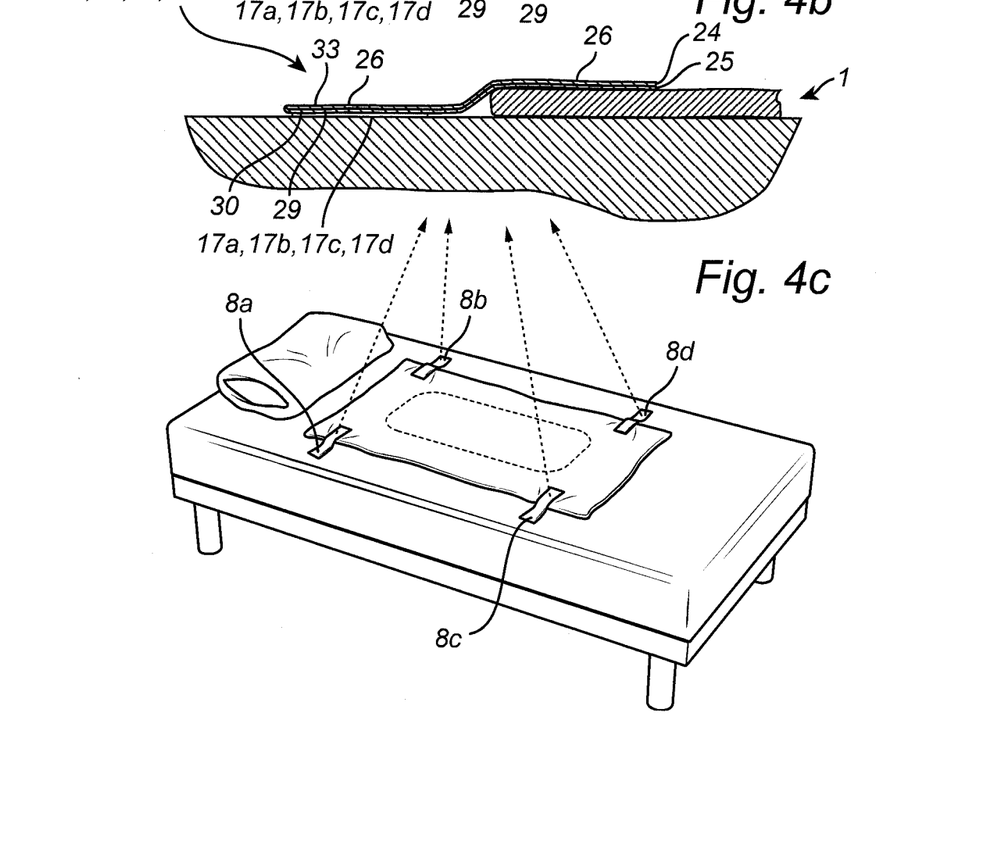

FIGS. 4*a*-4*c* illustrate schematically the steps of the fastening tabs 8*a-d* going from a package position as shown in FIG. 3 to be secured to a bed as a bed protector 1 and accordingly being in a first position.

FIG. 4*a* shows schematically a cross-sectional view of a fastening tab 8*a-d* being folded into a package position in accordance with FIG. 3. When the fastening tab 8*a-d* is in the package position and the care taker/nursing personnel is going to unfold the fastening tab 8*a-d* over the longitudinal side edges 9,10 of the article 1, to secure the article 1 to a bed or other supporting material, the care taker/nursing personnel will as a first step pull the third 18 and fourth 19 layer of the fastening tab 8*a-d* down in the z-direction as the arrow is indicating in the figure, and by this way release the third 18 and fourth 19 layer from the article 1 to achieve a fastening tab 8*a-d* being in a first position in accordance with FIG. 4*b*.

FIG. 4*b* shows schematically a cross-sectional view of a fastening tab 8*a-d* being unfolded from the package position to a first position. The third 18 and fourth 19 layer are unfolded around the longitudinal side edges 9, 10 of the article 1 creating a double-folded fastening tab 8*a-d* including a first layer 24 and a second layer 25 positioned below said first layer 24. The first layer 24 has a first surface 26 intended to face towards a user in that first position and the second layer 25 has a second surface 29 intended to face away from the user when the absorbent article 1 is in that first position. A fastening means 17*a*, 17*b*, 17*c*, or 17*d*, respectively, is arranged on the second surface 29 of the second layer 25 and is intended to fasten the article 1 to the bed. The fastening means 17*a*, 17*b*, 17*c*, or 17*d*, respectively, may be an adhesive or a mechanical fastening material. When the fastening tab 8*a-d* is in this first position, the first surface 30 of the third layer 18 is a subset of the second surface 29 of the second layer 25 and the second surface 33 of the fourth layer 19 is a subset of the first surface 26 of the first layer 24. When the fastening tab 8*a-d* is in the first position and the care taker/nursing personnel is going to secure the fastening tab 8*a-d* to a bed, the care taker/nursing personnel is pushing the fastening tab 8*a-d* so the fastening means 17*a-d*, respectively, will attach to the surface of the bed and hence affix the article 1 to the bed in accordance with FIG. 4*c*.

FIG. 4*c* shows schematically a cross-sectional view of a fastening tab 8*a-d* arranged to an article 1, the article 1 being in a first position attached to a bed. The fastening tab 8*a-d* is releasably attached to the surface of a bed by the fastening means 17*a-d*, respectively.

Figures 5, 6A, 6B:
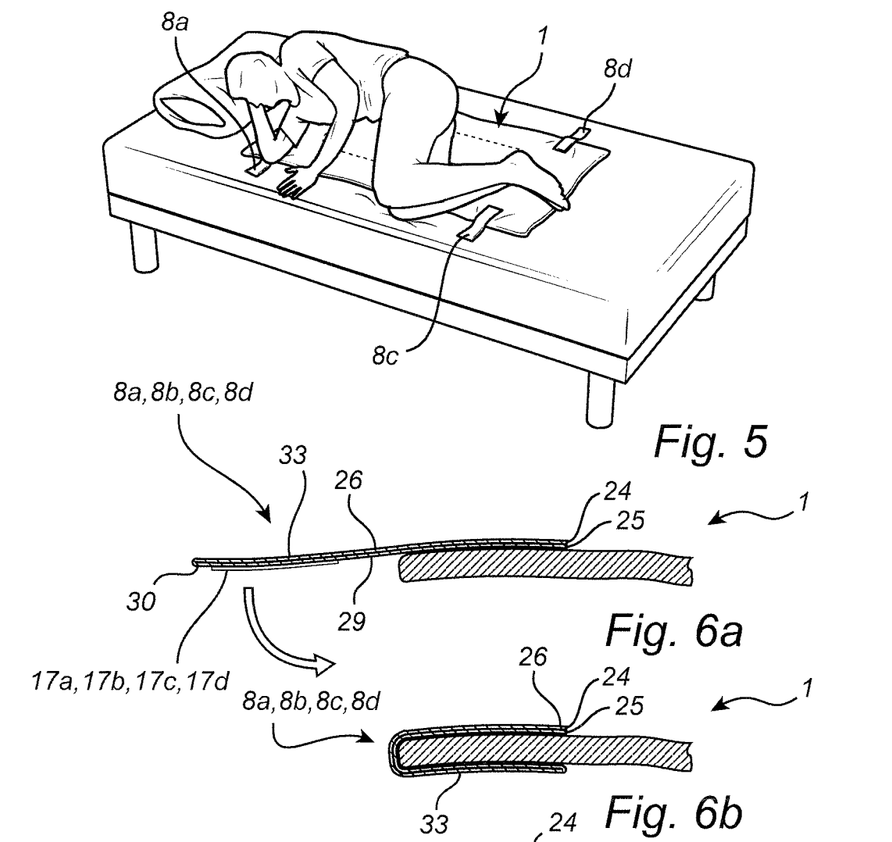
FIG. 5 shows schematically a perspective view of a bed protector being in a first position secured to a bed.
FIG. 6a shows schematically a cross-sectional view of a fastening tab being in a first position.
FIG. 6b shows schematically a cross-sectional view of a fastening tab being folded into a package position.

FIG. 5 shows schematically a perspective view of a bed protector 1 being in a first position attached to a bed and a user lying down on the bed. The fastening tabs 8*a-d* are releasably attached to the surface of the bed by the fastening means 17*a-d*, respectively.

FIGS. 6*a*-6*d* illustrate schematically the steps of the fastening tab 8*a-d* being in a first position and going to a second position that is a position for being attached to itself for secure the article 1 around the waist of a user.

FIG. 6*a* shows schematically a cross-sectional view of a fastening tab 8*a-d* being in a first position in accordance with FIG. 4*b*. When the fastening tab 8*a-d* is secured to the bed and the care taker/nursing personnel is going to attach the article 1 to itself around a waist of the user, for acting as a diaper 1, the care taker/nursing personnel will as a first step pull the fastening tab 8*a-d* upwardly in the z-direction, and by this way release the fastening tab 8*a-d* from the bed. As a second step, the care taker/nursing personnel then will fold the fastening tab 8*a-d* down around the longitudinal side edge 9, 10 of the article 1 as indicated by the arrow in the figure, the fastening tab 8a-d achieving a package position in accordance with FIG. 6b.

FIG. 6b shows schematically a cross-sectional view of a fastening tab 8a-d being folded into a package position in accordance with FIGS. 3 and 4a. Hence the fastening tab 8a-d is folded along the longitudinal side edges 9, 10 of the article and the first surface 30 of the third layer 18 having the fastening means 17a-d, respectively, is protected by the backsheet surface again. In this way, the fastening means 17a-d, respectively, is protected from sticking unintentionally to other surfaces such as the cloths of the wearer or other material. When the fastening tab 8a-d is in the package position and the care taker/nursing personnel is going to use the article 1 as a diaper and secure the article 1 around the waist of the wearer, she/he will unfold the first layer 24 of the fastening tab 8a-d as a first step in accordance with FIG. 6c.

Figure 6C:
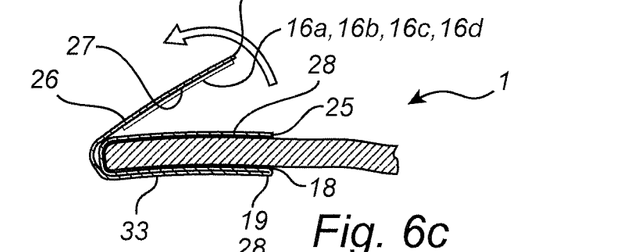
FIG. 6c shows schematically a cross-sectional view of a fastening tab wherein the first layer of the fastening tab is unfolded.

FIG. 6c shows schematically a cross-sectional view of a fastening tab 8a-d, wherein the first layer 24 of the fastening tab 8a-d is unfolded. The care taker/nursing personnel is pulling the first layer 24 upwardly in the z-direction, as indicated by the arrow in the figure and hence release the first layer 24 from the second layer 25 of the fastening tab 8a-d. Accordingly, the fastening means 16a-d, respectively, is uncovered from the first surface 28 of the second layer 25 and exposed and ready for engagement with the backsheet 6 of the article 1 in accordance with FIG. 6d.

Figure 6D:
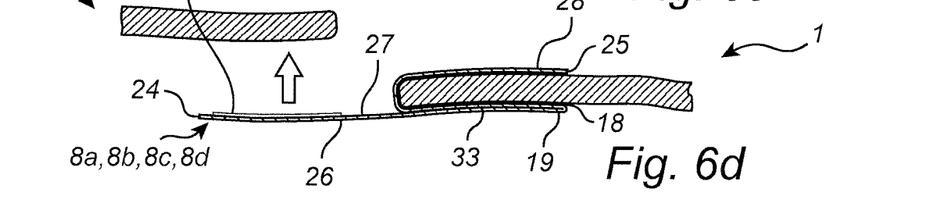
FIG. 6d shows schematically a cross-sectional view of a fastening tab, the first layer being unfolded and in a position ready for being attached to the backsheet of the absorbent article acting as a diaper.

FIG. 6d shows schematically a cross-sectional view of a fastening tab 8a-d, the first layer 24 is unfolded and in a position ready for being attached to the backsheet 6 of the absorbent article 1 acting as a diaper 1. The fastening means 16a-d, respectively, of the second surface 27 of the first layer 24 is attached to the backsheet 6 of the article 1. Hence, the article 1 is acting as a diaper 1 and is in the second position according to FIG. 7b.

Figure 7A:
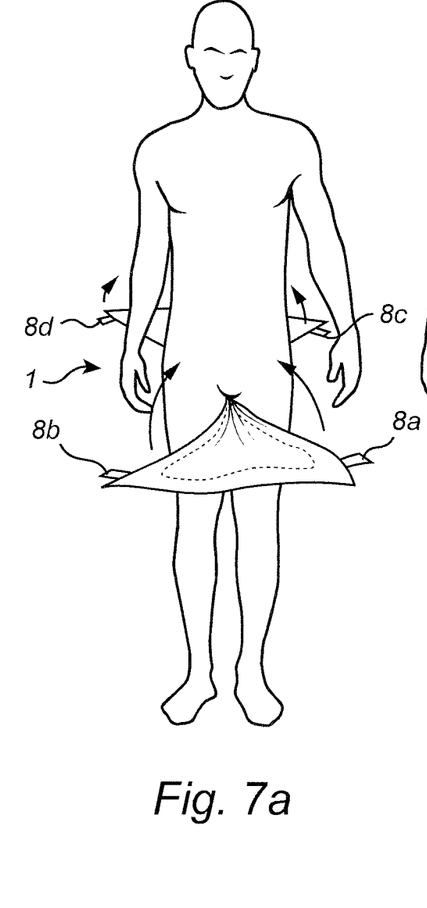
FIG. 7a illustrates schematically an absorbent article ready for being secured around a waist of a user.

FIG. 7a illustrates schematically an absorbent article 1 ready for being secured around a waist of a user.

Figure 7B:
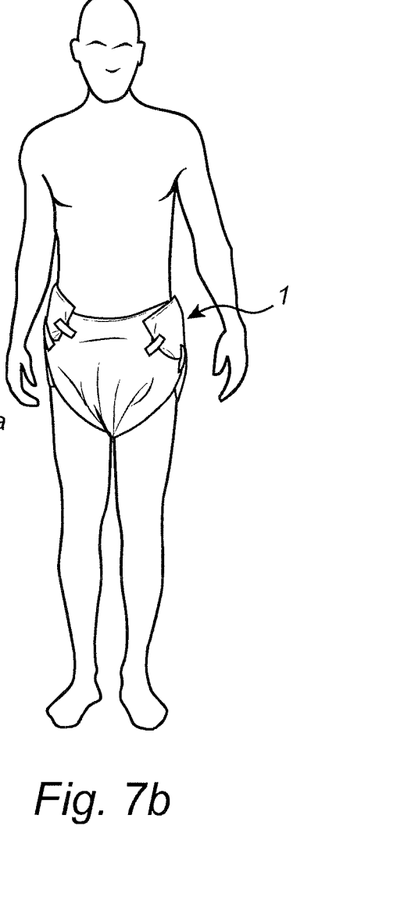
FIG. 7b illustrates schematically an absorbent article in a second position secured around the waist of a user.

FIG. 7b illustrates schematically an absorbent article 1 being in a second position secured around the waist of a user. The fastening means 16a-d, respectively, of the fastening tabs 8a-d is attached to the backsheet 6 of the diaper 1.

The invention claimed is:

1. An absorbent article having a longitudinal direction and a transverse direction, comprising:
    a front portion;
    a rear portion;
    a middle portion located between the rear portion and the front portion;
    a first longitudinal side edge;
    a second longitudinal side edge extending in said longitudinal direction;
    a first transverse side edge;
    a second transverse side edge extending in the transverse direction;
    a liquid permeable topsheet;
    a liquid impermeable backsheet;
    an absorbent core enclosed between the topsheet and the backsheet; and
    a first fastening tab and a second fastening tab attached to said article,
    wherein each of said first fastening tab and said second fastening tab has a first surface comprising a first fastener and a second surface comprising a second fastener,
    wherein at least one of said first fastening tab or said second fastening tab has a longitudinal direction of the tab extending in the transverse direction of the article and a transverse direction of the tab extending in the longitudinal direction of the article and a z-direction of the tab that is orthogonal to said longitudinal direction of the tab and said transverse direction of the tab,
    wherein said at least one of said first fastening tab or said second fastening tab has a first longitudinal side edge of the tab and a second longitudinal side edge of the tab extending in the longitudinal direction of the tab, and a first transverse side edge of the tab and a second transverse side edge of the tab extending in the transverse direction of the tab and a first imaginary line extending in the transverse direction of the tab,
    wherein said at least one of said first fastening tab or said second fastening tab has a first fold folded along a first imaginary line upwards in said z-direction forming a folded fastening tab with a portion of the first surface facing another portion of the first surface, said folded fastening tab comprising a first layer positioned on top of a second layer in said z-direction, and
    wherein said folded fastening tab folded along a second imaginary line downwards in said z-direction forms a double-folded fastening tab having a first layer positioned on top of a second layer in said z-direction, a third layer positioned below the second layer, and a fourth layer positioned below the third layer in said z-direction and with the third layer and the fourth layer being joined by the first fold along the first imaginary line.

2. The absorbent article according to claim 1, further comprising:
    a third fastening tab; and
    a fourth fastening tab attached to said article,
    wherein each of said third fastening tab and said fourth fastening tab has a first surface comprising a first fastener and a second surface comprising a second fastener.

3. The absorbent article according to claim 2, wherein at least one of said third fastening tab or said fourth fastening tab has a longitudinal direction of the tab extending in the transverse direction of the article and a transverse direction of the tab extending in the longitudinal direction of the article and a z-direction of the tab that is orthogonal to said longitudinal direction of the tab and said transverse direction of the tab,
    wherein said at least one of said third fastening tab or said fourth fastening tab fastening tab has a first longitudinal side edge of the tab and a second longitudinal side edge of the tab extending in the longitudinal direction of the tab, and a first transverse side edge of the tab and a second transverse side edge of the tab extending in the transverse direction of the tab and a first imaginary line extending in the transverse direction of the tab,
    wherein said at least one of said third fastening tab or said fourth fastening tab is folded along a first imaginary line upwards in said z-direction forming a folded fastening tab, said folded fastening tab comprising a first layer positioned on top of a second layer in said z-direction,
    wherein said first layer has a first surface intended to face towards a user when the absorbent article is in a first position and a second surface intended to face away from the user when the absorbent article is in a first position, and
    wherein said second layer has a first surface intended to face towards a user when the absorbent article is in a first position and a second surface intended to face away from the user when the absorbent article is in a first position.

4. The absorbent article according to claim 1, wherein at least one of said first fasteners or said second fasteners includes an adhesive.

5. The absorbent article according to claim 4, wherein at least one of said first fasteners or said second fasteners is covered by a release paper.

6. The absorbent article according to claim 1, wherein each of said first fasteners and said second fasteners includes an adhesive.

7. The absorbent article according to claim 1, wherein said first fasteners include a mechanical fastening material and said second fasteners include an adhesive.

8. The absorbent article according to claim 1, wherein at least one of said first fasteners or said second fasteners includes a mechanical fastening material.

9. The absorbent article according to claim 1, wherein, in said first position, said first fastener is between the first layer and the second layer in said z-direction.

10. The absorbent article according to claim 1, wherein, in said first position, said second fastener is between the second layer and the third layer in said z-direction.

* * * * *